US012640246B2

(12) United States Patent
Okuda

(10) Patent No.:     US 12,640,246 B2
(45) Date of Patent:          May 26, 2026

(54) PHARMACEUTICAL REFRIGERATOR OPERATION SUPPORT SYSTEM, PHARMACEUTICAL REFRIGERATOR OPERATION SUPPORT METHOD, AND NON-TRANSITORY COMPUTER-READABLE MEDIUM

(71) Applicant: PHC Holdings Corporation, Tokyo (JP)

(72) Inventor: Akinobu Okuda, Nara (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 243 days.

(21) Appl. No.: 18/452,368

(22) Filed: Aug. 18, 2023

(65) Prior Publication Data

US 2023/0395226 A1     Dec. 7, 2023

Related U.S. Application Data

(63) Continuation of application No. PCT/JP2022/004475, filed on Feb. 4, 2022.

(30) Foreign Application Priority Data

Mar. 1, 2021     (JP) ................................. 2021-031797

(51) Int. Cl.
*G16H 20/10*          (2018.01)
*G06Q 10/087*          (2023.01)
(52) U.S. Cl.
CPC ........... *G16H 20/10* (2018.01); *G06Q 10/087* (2013.01)
(58) Field of Classification Search
CPC .............................. G16H 20/10; G06Q 10/087
(Continued)

(56) References Cited

U.S. PATENT DOCUMENTS 6,225,904 B1 *   5/2001   Jaffe ..................... F25D 23/021
                                                340/545.6
11,282,028 B2 *   3/2022   Reid ...................... G06V 40/28
(Continued)

FOREIGN PATENT DOCUMENTS

GB          2566938  A  *   4/2019   ......... G07F 17/0092
JP     2007-181536  A       7/2007
(Continued)

OTHER PUBLICATIONS

Extended European Search Report dated Jun. 13, 2024 issued in the corresponding European Patent Application No. 22762896.3.
(Continued)

*Primary Examiner* — Michael Tomaszewski
(74) *Attorney, Agent, or Firm* — Rimon P.C.

(57)          ABSTRACT

A pharmaceutical refrigerator operation support system includes a server, a pharmaceutical refrigerator, a first computer that sends to the server information about a first medicine, information about a first RFID tag attached to the first medicine, and information about a first pharmaceutical distribution institution, and a second computer that sends to the server information about a second medicine, information about a second RFID tag attached to the second medicine, and information about a second pharmaceutical distribution institution. The server manages a status of medicine in the pharmaceutical refrigerator by identifying the first medicine as a medicine delivered by the first pharmaceutical distribution institution and identifying the second medicine as a medicine delivered by the second pharmaceutical distribution institution, based on information received from the pharmaceutical refrigerator, the first computer, and the second computer.

11 Claims, 4 Drawing Sheets

(58) Field of Classification Search

USPC ........................................................ 705/2–3

See application file for complete search history.

(56) References Cited

U.S. PATENT DOCUMENTS

| | | | | |
|---|---|---|---|---|
| 2006/0006999 A1* | 1/2006 | Walczyk | .................. | G06Q 10/08 340/572.1 |
| 2006/0124655 A1* | 6/2006 | Ratnakar | .................. | G07F 11/44 221/3 |
| 2008/0004908 A1* | 1/2008 | Oh | .................. | G16H 40/20 340/572.1 |
| 2008/0184719 A1* | 8/2008 | Lowenstein | .......... | G16Z 99/00 62/127 |
| 2010/0185458 A1* | 7/2010 | Newcomb | .............. | G16H 20/13 700/231 |
| 2010/0300130 A1* | 12/2010 | Shoenfeld | .............. | F25D 29/00 62/236 |
| 2011/0054668 A1* | 3/2011 | Holmes | .................. | G07F 11/60 221/210 |
| 2011/0181163 A1* | 7/2011 | Han | .................. | F25D 23/04 312/405 |
| 2011/0298587 A1* | 12/2011 | Walz | .................. | A61M 15/0028 340/10.1 |
| 2013/0006415 A1* | 1/2013 | Paydar | .................. | G16H 20/13 700/235 |
| 2013/0144435 A1* | 6/2013 | Czaplewski | .......... | G16H 20/13 700/241 |
| 2014/0155827 A1* | 6/2014 | Ostrander | .............. | G16H 10/65 604/93.01 |
| 2014/0165614 A1* | 6/2014 | Manning | .................. | F25D 29/00 62/62 |
| 2014/0316799 A1* | 10/2014 | Cosgrove | .......... | G07F 17/0092 705/2 |
| 2015/0127145 A1* | 5/2015 | Kim | .................. | G16H 40/67 700/235 |
| 2015/0148943 A1* | 5/2015 | Sullivan | .............. | A61J 7/0076 700/231 |
| 2016/0047583 A1* | 2/2016 | Lee | .................. | G06Q 10/06 62/132 |
| 2016/0350715 A1* | 12/2016 | Minvielle | .............. | A23L 5/15 |
| 2018/0121629 A1* | 5/2018 | Dyer | .................. | G06Q 40/08 |
| 2019/0139638 A1* | 5/2019 | Keefe | .................. | G16H 20/13 |
| 2020/0234380 A1* | 7/2020 | Dulori | .............. | G06Q 30/0283 |
| 2021/0161766 A1* | 6/2021 | Okuda | .................. | A61J 1/00 |
| 2022/0011042 A1* | 1/2022 | Cosgrove | .............. | G07F 17/12 |
| 2022/0238004 A1* | 7/2022 | Shoari | .................. | G01K 1/024 |
| 2023/0023992 A1* | 1/2023 | Yamaji | .................. | B65D 11/10 |
| 2023/0029147 A1* | 1/2023 | Morii | .................. | A61J 7/0472 |
| 2023/0395226 A1* | 12/2023 | Okuda | .................. | G16H 20/10 |

FOREIGN PATENT DOCUMENTS

| | | | | |
|---|---|---|---|---|
| JP | 2019-135632 A | 8/2019 | | |
| JP | 2019-135633 A | 8/2019 | | |
| JP | 6708342 B2 | 6/2020 | | |
| JP | 2020-184236 A | 11/2020 | | |
| WO | WO-0123816 A1 * | 4/2001 | .............. | E05F 15/43 |
| WO | WO-2016151594 A1 * | 9/2016 | .......... | G06Q 10/087 |
| WO | WO-2019057690 A1 * | 3/2019 | .......... | G16H 20/13 |
| WO | WO-2020031499 A1 * | 2/2020 | .......... | G06Q 10/087 |

OTHER PUBLICATIONS

Anonymous "RAIN RFID Smart Refrigerator for New Retail | Impinj+Stora Enso", , Feb. 1, 2019, XP093166926.

International Search Report dated May 17, 2022 issued in International Patent Application No. PCT/JP2022/004475, with English translation.

European Office Action dated Feb. 2, 2026 issued in the corresponding European Patent Application No. 22762896.3.

Ackley Sprague et al: "GS1 RFID/Barcode Interoperability Guideline", Nov. 1, 2016, XP093358694, pp. 1-45.

* cited by examiner

PHARMACEUTICAL REFRIGERATOR OPERATION SUPPORT SYSTEM, PHARMACEUTICAL REFRIGERATOR OPERATION SUPPORT METHOD, AND NON-TRANSITORY COMPUTER-READABLE MEDIUM

CROSS-REFERENCE OF RELATED APPLICATIONS

This application is a Continuation of International Patent Application No. PCT/JP2022/004475, filed on Feb. 4, 2022, which in turn claims the benefit of Japanese Patent Application No. 2021-031797, filed on Mar. 1, 2021, the entire disclosures of which Applications are incorporated by reference herein.

TECHNICAL FIELD

The present disclosure relates to a pharmaceutical refrigerator operation support system, a pharmaceutical refrigerator operation support method, and a non-transitory computer-readable medium.

BACKGROUND ART

Conventionally, medicines have been manufactured by pharmaceutical institutions and delivered to medical institutions through distribution institutions. In recent years, medicines that require strict temperature control have been distributed. Such medicines are managed by using pharmaceutical refrigerators in medical institutions. Literature disclosing related techniques includes, for example, PTL 1.

CITATION LIST

Patent Literature

PTL 1
Japanese Patent Application Laid-Open No. 2019-135632

SUMMARY OF INVENTION

Technical Problem

Usually, multiple distribution institutions deliver medicines to a single medical institution. Therefore, the medical institution needs to manage which distribution institutions have delivered which medicines. This is also true for medicines that require strict temperature control. In the case of medicines that require strict temperature control, it is also necessary to manage the temperature environment in which they have been stored. It is conceivable to utilize pharmaceutical refrigerators for such management. However, it has been difficult to manage various medicines by using a single pharmaceutical refrigerator, while identifying distribution institutions that have delivered the medicines.

In light of such circumstances, it is an object of the present disclosure to support a single pharmaceutical refrigerator in storing medicines delivered from multiple distribution institutions.

Solution to Problem

A pharmaceutical refrigerator operation support system according to the present disclosure includes: a server; a pharmaceutical refrigerator that is installed in a medical institution, obtains information from a radio frequency identification (RFID) tag attached to stored medicine, and sends information about a status of the stored medicine to the server; a first computer that sends to the server information about a first medicine, information about a first RFID tag attached to the first medicine, and information about a first pharmaceutical distribution institution that delivers the first medicine to the medical institution; and a second computer that sends to the server information about a second medicine, information about a second RFID tag attached to the second medicine, and information about a second pharmaceutical distribution institution that delivers the second medicine to the medical institution, in which the server manages a status of medicine in the pharmaceutical refrigerator by identifying the first medicine as a medicine delivered by the first pharmaceutical distribution institution and identifying the second medicine as a medicine delivered by the second pharmaceutical distribution institution, based on information received from the pharmaceutical refrigerator, the first computer, and the second computer.

A pharmaceutical refrigerator operation support method according to the present disclosure includes: sending, by a first computer to a server, information about a first medicine, information about a first radio frequency identification (RFID) tag attached to the first medicine, and information about a first pharmaceutical distribution institution that delivers the first medicine to a medical institution; sending, by a second computer to the server, information about a second medicine, information about a second RFID tag attached to the second medicine, and information about a second pharmaceutical distribution institution that delivers the second medicine to the medical institution; obtaining, by a pharmaceutical refrigerator installed in the medical institution, information from an RFID tag attached to medicine stored in the pharmaceutical refrigerator; sending, by the pharmaceutical refrigerator to the server, information obtained from the RFID tag attached to the medicine stored in the pharmaceutical refrigerator; and managing, by the server, a status of medicine in the pharmaceutical refrigerator by identifying the first medicine as a medicine delivered by the first pharmaceutical distribution institution and identifying the second medicine as a medicine delivered by the second pharmaceutical distribution institution, based on information received from the first computer, the second computer, and the pharmaceutical refrigerator.

A non-transitory computer-readable medium according to the present disclosure is a medium storing a computer program executed by a server communicably connected via a network to a pharmaceutical refrigerator that is installed in a medical institution and that stores medicine delivered by a first pharmaceutical distribution institution and a second pharmaceutical distribution institution, the computer program causing the server to execute: receiving, from a first computer, information about a first medicine, information about a first radio frequency identification (RFID) tag attached to the first medicine, and information about the first pharmaceutical distribution institution; receiving, from a second computer, information about a second medicine, information about a second RFID tag attached to the second medicine, and information about the second pharmaceutical distribution institution; receiving, from the pharmaceutical refrigerator, information obtained from an RFID tag affixed to medicine stored in the pharmaceutical refrigerator; and managing a status of medicine in the pharmaceutical refrigerator by identifying the first medicine as a medicine delivered by the first pharmaceutical distribution institution and identifying the second medicine as a medicine delivered by the second pharmaceutical distribution institution, based on information received from the first computer, the second computer, and the pharmaceutical refrigerator.

Advantageous Effects of Invention

According to the present disclosure, a single pharmaceutical refrigerator can be supported in storing medicines delivered from multiple distribution institutions.

DESCRIPTION OF EMBODIMENTS

Hereinafter, embodiments of the present disclosure will be described in detail with reference to the drawings. Note that the embodiments described hereinafter are examples, and the present disclosure is not limited by these embodiments.

Embodiment 1

Figure 1:
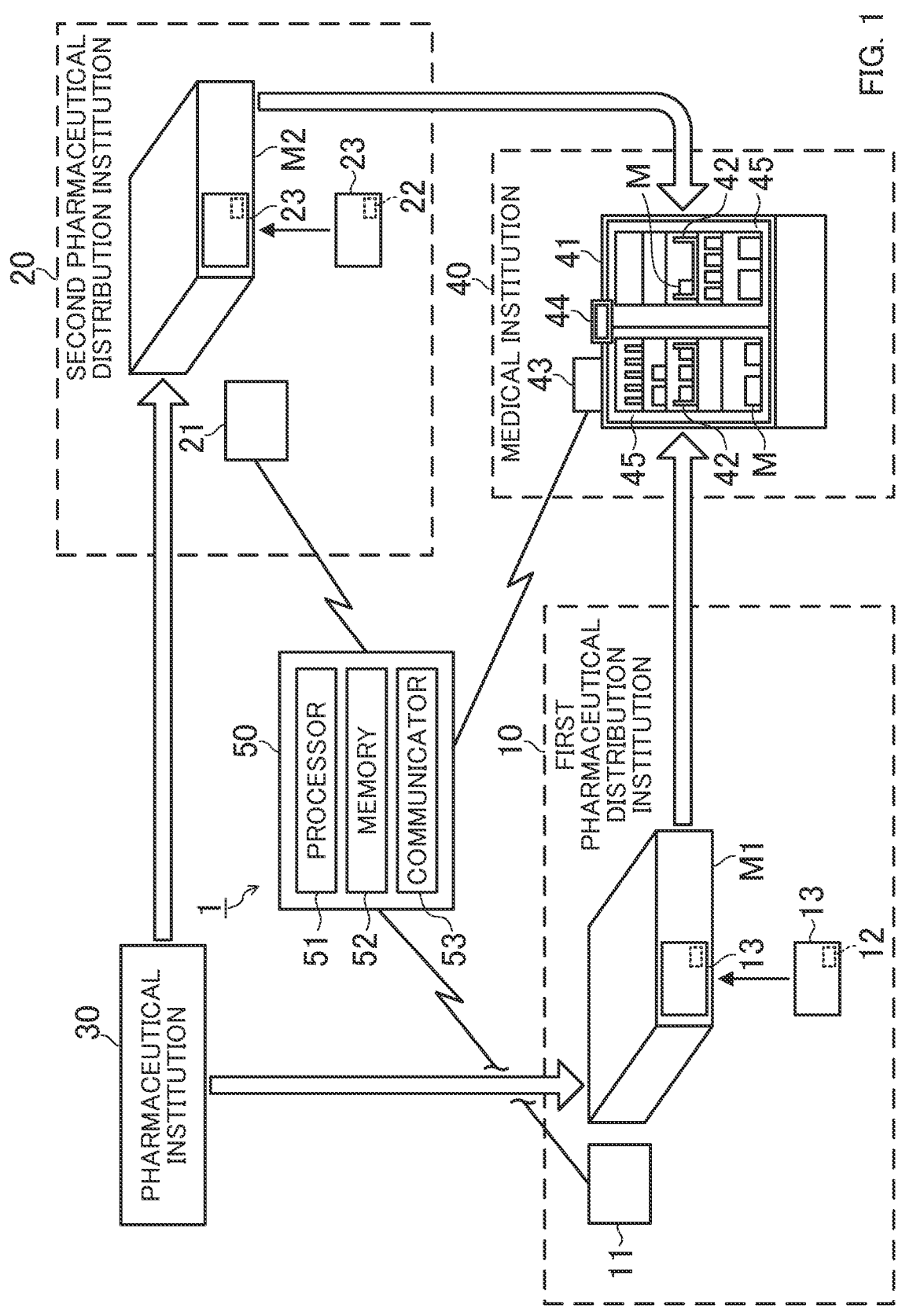
FIG. 1 is a diagram illustrating an example of the configuration of a pharmaceutical refrigerator operation support system according to Embodiment 1.

FIG. 1 is a diagram illustrating the configuration of pharmaceutical refrigerator operation support system 1 according to Embodiment 1.

FIG. 1 also illustrates how medicine M is distributed. That is, medicine M (including first medicine M1 and second medicine M2) manufactured at pharmaceutical institution 30 is delivered to medical institution 40 via pharmaceutical distribution institutions (including first pharmaceutical distribution institution 10 and second pharmaceutical distribution institution 20). Specifically, first medicine M1 manufactured by pharmaceutical institution 30 is delivered to medical institution 40 via first pharmaceutical distribution institution 10. In addition, second medicine M2 manufactured by pharmaceutical institution 30 is delivered to medical institution 40 via second pharmaceutical distribution institution 20.

For the convenience of description, first medicine M1 is described as one medicine in the present specification, but it should be understood that first medicine M1 may include multiple medicines. In addition, if first medicine M1 includes multiple medicines, the multiple first medicines M1 may be delivered to medical institution 40 at one time, or may be delivered in multiple times. For example, when the inventory of first medicine M1 at medical institution 40 runs out or is about to run out, the next first medicine M1 may be delivered. The same is true for second medicine M2.

Moreover, for the convenience of description, in the present specification, pharmaceutical distribution institutions are described as the total of two pharmaceutical distribution institutions, first pharmaceutical distribution institution 10 and second pharmaceutical distribution institution 20, but it should be understood that the number of pharmaceutical distribution institutions is not limited to two. For example, it is included in the technical scope of the present disclosure that there are multiple second pharmaceutical distribution institutions 20.

Note that pharmaceutical institution 30 is, for example, a pharmaceutical manufacturer. The distribution institutions are, for example, wholesalers. Medical institution 40 is, for example, a hospital or a pharmacy. In addition, pharmaceutical institution 30 manufacturing first medicine M1 and pharmaceutical institution 30 manufacturing second medicine M2 may be the same pharmaceutical institution or may be pharmaceutical institutions that are different from each other. In the case where first medicine M1 or second medicine M2 includes multiple medicines, first medicines M1 or second medicines M2 may be manufactured at pharmaceutical institutions 30 that are different from each other.

In the present embodiment, pharmaceutical refrigerator operation support system 1 includes first computer 11, second computer 21, pharmaceutical refrigerator 41, and server 50.

First computer 11 is installed in first pharmaceutical distribution institution 10. First computer 11 includes an arithmetic processor such as a central processing unit (CPU), a storage apparatus such as a read only memory (ROM), a random access memory (RAM), and a hard disk drive (HDD), and a communication apparatus such as a network interface card that communicates with server 50 via a communication network.

First computer 11 is communicably connected to server 50 via a communication network. First computer 11 sends information about first pharmaceutical distribution institution 10 to server 50 when starting communication with server 50 or when requesting server 50 to authenticate first computer 11 or the user of first computer 11. The information about first pharmaceutical distribution institution 10 is, for example, the identification information of first computer 11, the identification information of an application executed by first computer 11, or the identification information of the user of first computer 11. Note that first computer 11 may send the information about first pharmaceutical distribution institution 10 to server 50 when sending information about first medicine M1 or information about first radio frequency identification (RFID) tag 12, which will be described later. Second computer 21 is installed in second pharmaceutical distribution institution Second computer 21 includes an arithmetic processor such as a CPU, a storage apparatus such as a ROM, a RAM, and an HDD, and a communication apparatus such as a network interface card that communicates with server 50 via a communication network.

Second computer 21 is communicably connected to server 50 via a communication network. Second computer 21 sends information about second pharmaceutical distribution institution 20 to server 50 when starting communication with server 50 or when requesting server 50 to authenticate second computer 21 or the user of second computer 21. The information about second pharmaceutical distribution institution 20 is, for example, the identification information of second computer 21, the identification information of an application executed by second computer 21, or the identification information of the user of second computer 21. Note that second computer 21 may send the information about second pharmaceutical distribution institution 20 to server 50 when sending information about second medicine M2 or information about second RFID tag 22, which will be described later.

Pharmaceutical refrigerator 41 is installed in medical institution 40. Inside pharmaceutical refrigerator 41, removable cage 42 is placed. Cage 42 has an antenna for obtaining information from an RFID tag attached to medicine M placed inside cage 42. Pharmaceutical refrigerator 41 has communication apparatus 43. Communication apparatus 43 is communicably connected to server 50 via a communication network. Operation display apparatus 44 is attached on the front surface of pharmaceutical refrigerator 41. Operation display apparatus 44 is used by individuals who store medicine in pharmaceutical refrigerator 41 or retrieve medicine from pharmaceutical refrigerator 41 to perform operations such as user login and logout, as well as medicine storage and retrieval operations. Pharmaceutical refrigerator 41 is configured to be able to store and retrieve medicine M by opening and closing sliding door 45. Note that operation display apparatus 44 may accept a chamber temperature setting operation, or may present information such as the quantity of medicine M in stock or the chamber temperature to the user. Cage 42, communication apparatus 43, and operation display apparatus 44 are also configured to be attached as retrofit apparatuses to existing pharmaceutical refrigerator 41 not equipped with them.

Pharmaceutical refrigerator 41 includes a refrigeration circuit and a chamber temperature sensor (not illustrated), and can maintain the chamber temperature at a temperature set by the user. Pharmaceutical refrigerator 41 can also record the time and the chamber temperature at that time in association with each other. Pharmaceutical refrigerator 41 can also detect that medicine M has been placed in cage 42 and retrieved from cage 42. Therefore, pharmaceutical refrigerator 41 can obtain the time at which medicine M is stored in pharmaceutical refrigerator 41 and the time at which medicine M is retrieved from pharmaceutical refrigerator 41. Pharmaceutical refrigerator 41 can also record and manage the temperature at which medicine M has been stored from the time it is stored until the time it is retrieved.

Server 50 is a computer including processor 51, memory 52, and communicator 53. Processor 51 includes an arithmetic processor such as a CPU. Memory 52 includes a storage apparatus such as a ROM, a RAM, and an HDD. Communicator 53 includes a communication apparatus such as a network interface card that communicates with first computer 11, second computer 21, and pharmaceutical refrigerator 41 via a communication network. By executing a computer program stored in memory 52 by processor 51 and communicating with first computer 11, second computer 21, and pharmaceutical refrigerator 41 by communicator 53, a pharmaceutical refrigerator operation support method according to the present disclosure is executed.

Figure 2:
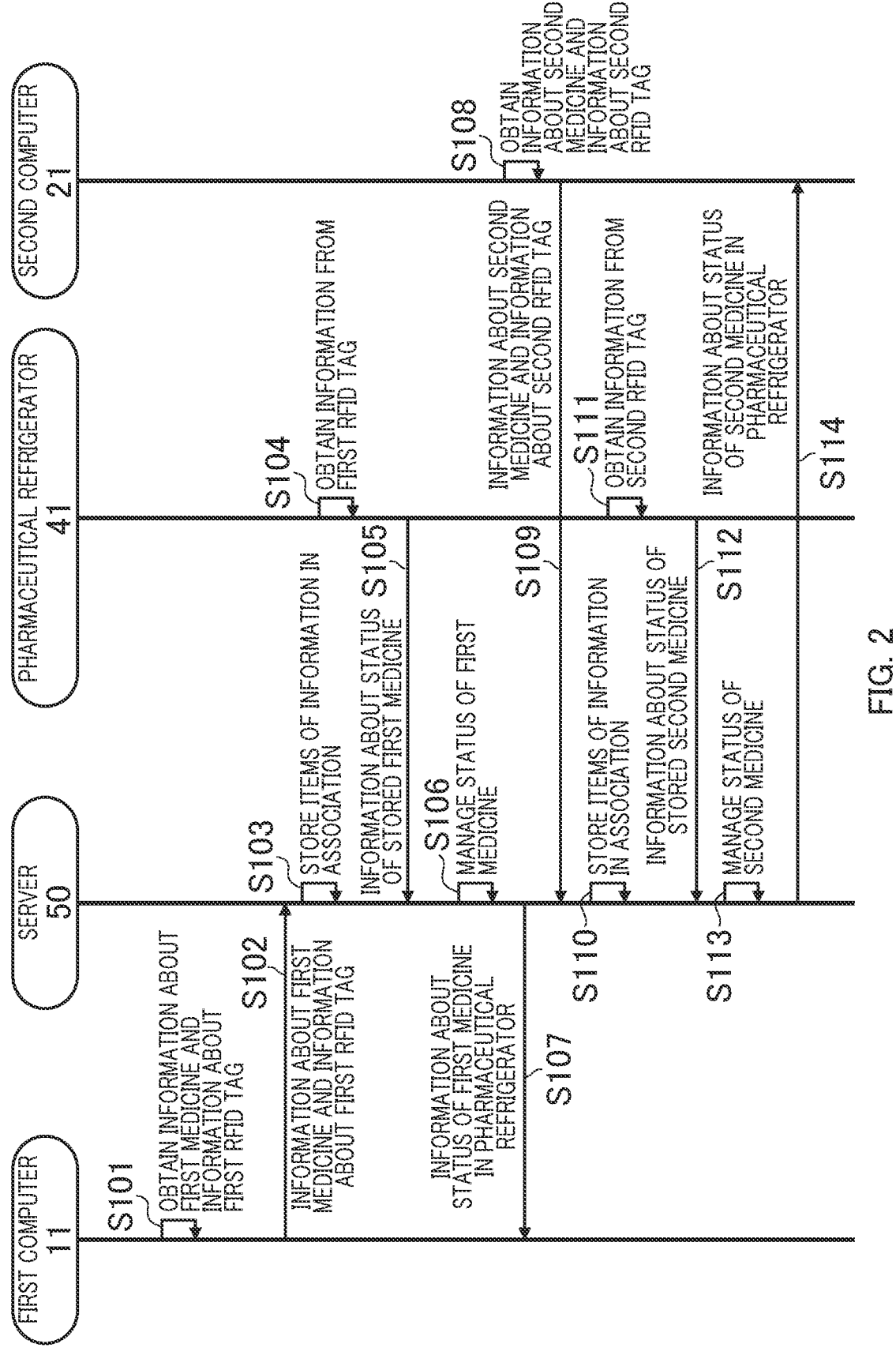
FIG. 2 is a sequential diagram illustrating the flow of the pharmaceutical refrigerator operation support system according to Embodiment 1.

FIG. 2 is a sequential diagram illustrating an example of the flow of a pharmaceutical refrigerator operation support method executed by pharmaceutical refrigerator operation support system 1 according to the present embodiment.

When first medicine M1, which is a medicine that requires strict temperature control, is delivered from pharmaceutical institution 30 to first pharmaceutical distribution institution 10, first medicine M1 is attached with first RFID tag 12. The method for attaching first RFID tag 12 is not particularly limited, and, for example, first RFID tag 12 may be attached by affixing first label 13 to which first RFID tag 12 is attached in advance to first medicine M1. When affixing first label 13 to first medicine M1, it is preferable to affix it so as to be perpendicular to the ground plane of the outer box of first medicine M1. In addition, if first medicine M1 is printed with information that can identify what kind of medicine first medicine M1 is (for example, first indication 14 in FIG.

3), it is preferable to affix first label 13 on a face where this information is not printed. Note that FIG. 1 illustrates a situation where first label 13 having first RFID tag 12 is affixed to the surface of first medicine M1.

First computer 11 obtains information about first medicine M1 and information about first RFID tag 12 (S101). First computer 11 may obtain these items of information in any way, such as by receiving information input by the user of first computer 11 using an input apparatus such as a keyboard. The information about first medicine M1 is information that can identify what kind of medicine first medicine M1 is, such as an identification number unique to first medicine M1. The information about first RFID tag 12 is information that can be associated one-to-one with information that can be obtained from first RFID tag 12 through wireless communication, such as an identification number unique to first RFID tag 12.

Next, first computer 11 sends the information about first medicine M1 and the information about first RFID tag 12 to server 50 (S102). Upon receiving these items of information from first computer 11, server 50 stores the aforementioned information about first pharmaceutical distribution institution 10, information about first medicine M1, and information about first RFID tag 12 in memory 52 in association with one another (S103). A database for managing the name, quantity in stock, storage temperature history, supplier, and the like of medicine M stored in pharmaceutical refrigerator 41 may be constructed in memory 52, and information may be stored by registering the information in the database.

Meanwhile or thereafter, first medicine M1 is delivered to medical institution 40 by first pharmaceutical distribution institution 10. Upon delivery to medical institution 40, first medicine M1 is stored in pharmaceutical refrigerator 41. At this time, first medicine M1 is placed in cage 42.

Pharmaceutical refrigerator 41 then obtains information from first RFID tag 12 by wireless communication via the antenna of cage 42 (S104). The information obtained at this time is, for example, the identification number of first RFID tag 12. Next, pharmaceutical refrigerator 41 sends information about the status of first medicine M1 to server 50 (S105). The information about the status of first medicine M1 includes the information obtained from first RFID tag 12, as well as information about the date and time of storage, date and time of retrieval, quantity in stock, storage temperature, and the like of a medicine to which first RFID tag 12 is attached (i.e., first medicine M1).

Upon obtaining the information from pharmaceutical refrigerator 41, server 50 stores these items of information in memory 52 and manages them (S106). The storage of information may be done by registering the information in the database constructed in memory 52. At this time, server 50 checks the information about first RFID tag 12 received from first computer 11 against the information received from pharmaceutical refrigerator 41, that is, the information obtained by pharmaceutical refrigerator 41 from first RFID tag 12. This allows server 50 to identify that medicine M stored in pharmaceutical refrigerator 41 is first medicine M1 delivered by first pharmaceutical distribution institution 10.

If necessary, server 50 may send the information about the status of first medicine M1 to first computer 11 (S107). This allows first pharmaceutical distribution institution 10 to know whether first medicine M1 is managed in medical institution 40 in an appropriate temperature environment, the quantity of first medicine M1 in stock, and the like, and to provide appropriate services to medical institution 40. The sending of information from server 50 to first computer 11 may be performed automatically or may be performed in response to a request from first computer 11. In the case where the sending of information is performed automatically, the sending may be performed every certain time or may be performed each time sliding door 45 is opened and closed, where it is highly likely that medicine M has been stored or retrieved.

Also, upon delivery of second medicine M2, which is a medicine that requires strict temperature control, from pharmaceutical institution 30 to second pharmaceutical distribution institution 20, second RFID tag 22 is attached to second medicine M2. The method for attaching second RFID tag 22 is not particularly limited, and, for example, second RFID tag 22 may be attached by affixing second label 23 to which second RFID tag 22 is attached in advance to second medicine M2. When affixing second label 23 to second medicine M2, it is preferable to affix it so as to be perpendicular to the ground plane of the outer box of second medicine M2. In addition, if second medicine M2 is printed with information that can identify what kind of medicine second medicine M2 is (for example, second indication 24 in FIG. 3), it is preferable to affix second label 23 on a face where this information is not printed. Note that FIG. 1 illustrates a situation where second label 23 having second RFID tag 22 is affixed to the surface of second medicine M2.

Second computer 21 obtains information about second medicine M2 and information about second RFID tag 22 (S108). Second computer 21 may obtain these items of information in any way, such as by receiving information input by the user of second computer 21 using an input apparatus such as a keyboard. The information about second medicine M2 is information that can identify what kind of medicine second medicine M2 is, such as an identification number unique to second medicine M2. The information about second RFID tag 22 is information that can be associated one-to-one with information that can be obtained from second RFID tag 22 through wireless communication, such as an identification number unique to second RFID tag 22.

Next, second computer 21 sends the information about second medicine M2 and the information about second RFID tag 22 to server 50 (S109). Upon receiving these items of information from second computer 21, server 50 stores the aforementioned information about second pharmaceutical distribution institution 20, information about second medicine M2, and information about second RFID tag 22 in memory 52 in association with one another (S110). The storage of information may be done by registering the information in the database constructed in memory 52.

Meanwhile or thereafter, second medicine M2 is delivered to medical institution 40 by second pharmaceutical distribution institution 20. Upon delivery to medical institution second medicine M2 is stored in pharmaceutical refrigerator 41. At this time, second medicine M2 is placed in cage 42.

Pharmaceutical refrigerator 41 then obtains information from second RFID tag 22 by wireless communication via the antenna of cage 42 (S111). The information obtained at this time is, for example, the identification number of second RFID tag 22. Next, pharmaceutical refrigerator 41 sends information about the status of second medicine M2 to server 50 (S112). The information about the status of second medicine M2 includes the information obtained from second RFID tag 22, as well as information about the date and time of storage, date and time of retrieval, quantity in stock, storage temperature, and the like of the medicine to which second RFID tag 22 is attached (i.e., second medicine M2).

Upon obtaining the information from pharmaceutical refrigerator 41, server 50 stores these items of information in memory 52 and manages them (S113). The storage of information may be done by registering the information in the database constructed in memory 52. At this time, server 50 checks the information about second RFID tag 22 received from second computer 21 against the information received from pharmaceutical refrigerator 41, that is, the information obtained by pharmaceutical refrigerator 41 from second RFID tag 22. This allows server 50 to identify that medicine M stored in pharmaceutical refrigerator 41 is second medicine M2 delivered by second pharmaceutical distribution institution 20.

If necessary, server 50 may send the information about the status of second medicine M2 to second computer 21 (S114). This allows second pharmaceutical distribution institution 20 to know whether second medicine M2 is managed in medical institution 40 in an appropriate temperature environment, the quantity of second medicine M2 in stock, and the like, and to provide appropriate services to medical institution 40. The sending of information from server 50 to second computer 21 may be performed automatically or may be performed in response to a request from second computer 21. In the case where the sending of information is performed automatically, the sending may be performed every certain time or may be performed each time sliding door 45 is opened and closed, where it is highly likely that medicine M has been stored or retrieved.

Pharmaceutical refrigerator operation support system 1 according to the present embodiment is configured and functions as described above. Therefore, server 50 can identify and manage which distributor, specifically either first pharmaceutical distribution institution 10 or second pharmaceutical distribution institution 20, has delivered medicine M stored in pharmaceutical refrigerator 41. Accordingly, upon inquiry from first pharmaceutical distribution institution 10, second pharmaceutical distribution institution 20, and medical institution 40, the storage status such as the storage temperature and the supplier of each medicine M can be reported. In other words, single pharmaceutical refrigerator 41 can be shared by multiple distribution institutions. That is, single pharmaceutical refrigerator 41 can be supported in storing medicine M delivered from multiple distribution institutions while identifying the supplier. Note that only individuals with specific authority (such as the administrator of medical institution 40) may have access to information about which medicines have been delivered by whom. In addition, the administrator of first pharmaceutical distribution institution 10 may have access to information about first medicine M1, but may not have access to information about second medicine M2, and the administrator of second pharmaceutical distribution institution 20 may have access to information about second medicine M2, but may not have access to information about first medicine M1. It should be understood that multiple pharmaceutical refrigerators 41 may be installed in medical institution 40.

Embodiment 2

Figure 3:
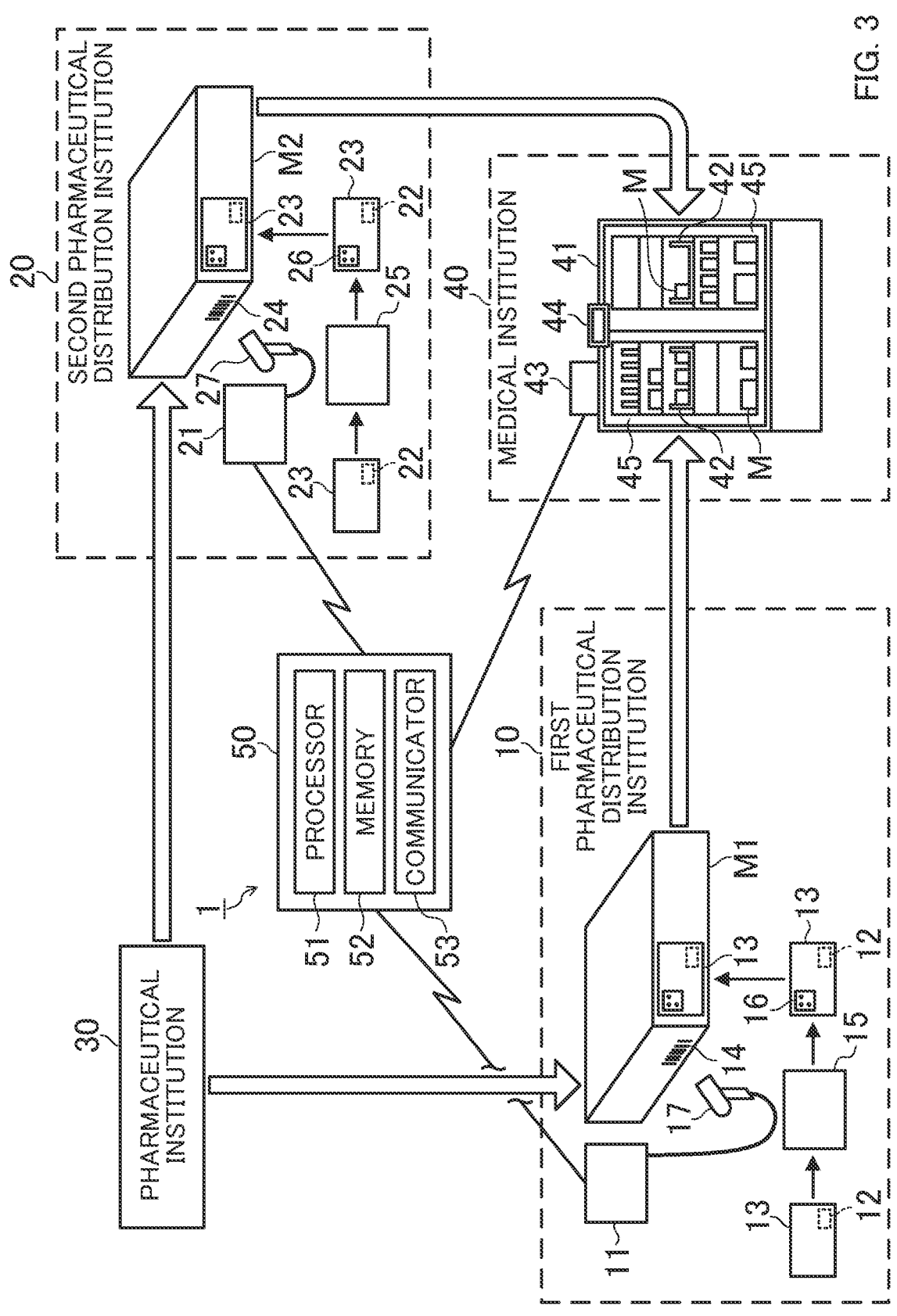
FIG. 3 is a diagram illustrating an example of the configuration of a pharmaceutical refrigerator operation support system according to Embodiment 2.

FIG. 3 is a diagram illustrating the configuration of pharmaceutical refrigerator operation support system 1 according to Embodiment 2. Hereinafter, descriptions of matters common to Embodiment 1 may be omitted.

On the surface of medicine M manufactured at pharmaceutical institution 30, indication with information about medicine M is printed. For example, first indication 14 is printed on the surface of first medicine M1, and second indication 24 is printed on the surface of second medicine M2. These indications may be in the form of, for example, bar codes or two-dimensional codes, or they may be character strings. Information about medicine M is information that can identify what kind of medicine medicine M is, such as an identification number unique to medicine M.

In the present embodiment, pharmaceutical refrigerator operation support system 1 is configured of first computer 11, first printer 15, first scanner 17, second computer 21, second printer 25, second scanner 27, pharmaceutical refrigerator 41, and server 50.

First printer 15 is installed in first pharmaceutical distribution institution 10. First printer 15 is configured to be able to obtain information about first RFID tag 12 from first RFID tag 12 by wirelessly communicating with first RFID tag 12. In addition, first printer is configured to be able to print, on first label 13, first code 16 including information corresponding one-to-one with information about first RFID tag 12. FIG. 3 illustrates a situation where first label 13 having first RFID tag 12 is supplied to first printer 15, first code 16 is printed on the surface of first label 13, and then first label 13 is affixed to the surface of first medicine M1.

First scanner 17 is installed in first pharmaceutical distribution institution 10. First scanner 17 is configured to be able to obtain information from first indication 14 and first code 16. First scanner 17 is also configured to be able to pass the obtained information to first computer 11.

Second printer 25 is installed in second pharmaceutical distribution institution 20. Second printer 25 is configured to be able to obtain information about second RFID tag 22 from second RFID tag 22 by wirelessly communicating with second RFID tag 22. In addition, second printer 25 is configured to be able to print, on second label 23, second code 26 including information corresponding one-to-one with information about second RFID tag 22. FIG. 3 illustrates a situation where second label 23 having second RFID tag 22 is supplied to second printer 25, second code 26 is printed on the surface of second label 23, and then second label 23 is affixed to the surface of second medicine M2.

Second scanner 27 is installed in second pharmaceutical distribution institution 20. Second scanner 27 is configured to be able to obtain information from second indication 24 and second code 26. Second scanner 27 is also configured to be able to pass the obtained information to second computer 21.

Pharmaceutical refrigerator 41 according to the present embodiment is one installed in medical institution 40 by first pharmaceutical distribution institution 10. Note that, as a matter of course, the installation of pharmaceutical refrigerator 41 in the present specification includes the installation of pharmaceutical refrigerator 41 equipped with cage 42, communication apparatus 43, and operation display apparatus 44, and further includes the attaching of cage 42, communication apparatus 43, and operation display apparatus 44 as retrofit apparatuses to existing pharmaceutical refrigerator 41 not equipped with cage 42, communication apparatus 43, or operation display apparatus 44. That is, the installer in the present embodiment includes individuals who have installed pharmaceutical refrigerator 41 equipped with cage 42, communication apparatus 43, and operation display apparatus 44, as well as individuals who have attached cage 42, communication apparatus 43, and operation display apparatus 44 as retrofit apparatuses to existing pharmaceutical refrigerator 41 not equipped with cage 42, communication apparatus 43, or operation display apparatus 44.

Figure 4:
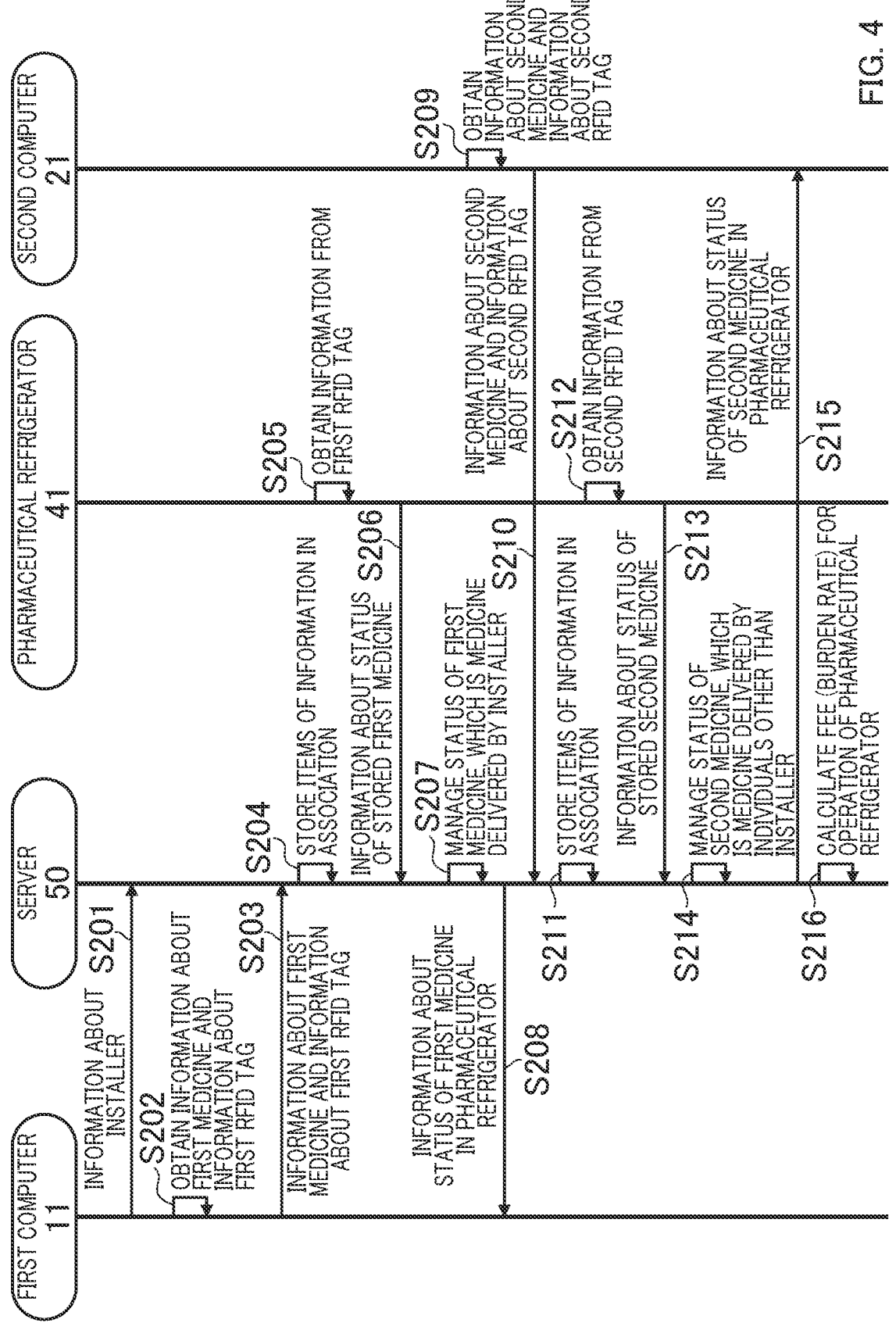
FIG. 4 is a sequential diagram illustrating the flow of the pharmaceutical refrigerator operation support system according to Embodiment 2.

FIG. 4 is a sequential diagram illustrating an example of the flow of a pharmaceutical refrigerator operation support method executed by pharmaceutical refrigerator operation support system 1 according to the present embodiment.

Server 50 obtains the installer information indicating that the installer who has installed pharmaceutical refrigerator 41 is first pharmaceutical distribution institution 10 (S201). As illustrated in FIG. 4, the installer information may be sent from first computer 11, may be directly input to server 50 by the operator of server 50, or may be sent from outside pharmaceutical refrigerator operation support system 1.

When first medicine M1, which is a medicine that requires strict temperature control, is delivered from pharmaceutical institution 30 to first pharmaceutical distribution institution 10, first medicine M1 is attached with first RFID tag 12. Specifically, after first code 16 is printed by first printer 15 on first label 13 to which first RFID tag 12 is attached in advance, first label 13 is affixed to first medicine M1.

First computer 11 obtains information about first medicine M1 and information about first RFID tag 12 by reading first indication 14 and first code 16 using first scanner 17 (S202).

Next, first computer 11 sends the information about first medicine M1 and the information about first RFID tag 12 to server 50 (S203). Upon receiving these items of information from first computer 11, server 50 stores the information about first pharmaceutical distribution institution 10, the information about first medicine M1, and the information about first RFID tag 12, which are described in Embodiment 1, in memory 52 in association with one another (S204).

Meanwhile or thereafter, first medicine M1 is delivered to medical institution 40 by first pharmaceutical distribution institution 10. Upon delivery to medical institution 40, first medicine M1 is stored in pharmaceutical refrigerator 41. At this time, first medicine M1 is placed in cage 42.

Pharmaceutical refrigerator 41 then obtains information from first RFID tag 12 by wireless communication via the antenna of cage 42 (S205). The information obtained at this time is, for example, the identification number of first RFID tag 12. Next, pharmaceutical refrigerator 41 sends information about the status of first medicine M1 to server 50 (S206). The information about the status of first medicine M1 includes the information obtained from first RFID tag 12, as well as information about the date and time of storage, date and time of retrieval, quantity in stock, storage temperature, and the like of a medicine to which first RFID tag 12 is attached (i.e., first medicine M1).

Upon obtaining the information from pharmaceutical refrigerator 41, server 50 stores these items of information in memory 52 and manages them (S207). At this time, server 50 checks the information about first RFID tag 12 received from first computer 11 against the information received from pharmaceutical refrigerator 41, that is, the information obtained by pharmaceutical refrigerator 41 from first RFID tag 12. This allows server 50 to identify that medicine M stored in pharmaceutical refrigerator 41 is first medicine M1 delivered by first pharmaceutical distribution institution 10. Furthermore, server 50 can store the information in a state where it can be identified that first medicine M1 is a medicine delivered by the installer who has installed pharmaceutical refrigerator 41, by means such as flagging the information about first medicine M1 based on the installer information. In other words, server 50 can manage first medicine M1 delivered by first pharmaceutical distribution institution 10 as being identified as a medicine delivered by first pharmaceutical distribution institution 10, who is the installer, based on the information received from pharmaceutical refrigerator 41 and first computer 11, as well as the installer information.

If necessary, server 50 may send the information about the status of first medicine M1 to first computer 11 (S208). This allows first pharmaceutical distribution institution 10 to know whether first medicine M1 is managed in medical institution 40 in an appropriate temperature environment, the quantity of first medicine M1 in stock, and the like, and to provide appropriate services to medical institution 40. The sending of information from server 50 to first computer 11 may be performed automatically or may be performed in response to a request from first computer 11. In the case where the sending of information is performed automatically, the sending may be performed every certain time or may be performed each time sliding door 45 is opened and closed, where it is highly likely that medicine M has been stored or retrieved.

Also, upon delivery of second medicine M2, which is a medicine that requires strict temperature control, from pharmaceutical institution 30 to second pharmaceutical distribution institution 20, second RFID tag 22 is attached to second medicine M2. Specifically, after second code 26 is printed by second printer 25 on second label 23 to which second RFID tag 22 is attached in advance, second label 23 is affixed to second medicine M2.

Second computer 21 obtains information about second medicine M2 and information about second RFID tag 22 by reading second indication 24 and second code 26 using second scanner 27 (S209).

Next, second computer 21 sends the information about second medicine M2 and the information about second RFID tag 22 to server 50 (S210). Upon receiving these items of information from second computer 21, server 50 stores the information about second pharmaceutical distribution institution 20, the information about second medicine M2, and the information about second RFID tag 22, which are described in Embodiment 1, in memory 52 in association with one another (S211).

Meanwhile or thereafter, second medicine M2 is delivered to medical institution 40 by second pharmaceutical distribution institution 20. Upon delivery to medical institution second medicine M2 is stored in pharmaceutical refrigerator 41. At this time, second medicine M2 is placed in cage 42.

Pharmaceutical refrigerator 41 then obtains information from second RFID tag 22 by wireless communication via the antenna of cage 42 (S212). The information obtained at this time is, for example, the identification number of second RFID tag 22. Next, pharmaceutical refrigerator 41 sends information about the status of second medicine M2 to server 50 (S213). The information about the status of second medicine M2 includes the information obtained from second RFID tag 22, as well as information about the date and time of storage, date and time of retrieval, quantity in stock, storage temperature, and the like of the medicine to which second RFID tag 22 is attached (i.e., second medicine M2).

Upon obtaining the information from pharmaceutical refrigerator 41, server 50 stores these items of information in memory 52 and manages them (S214). At this time, server 50 checks the information about second RFID tag 22 received from second computer 21 against the information received from pharmaceutical refrigerator 41, that is, the information obtained by pharmaceutical refrigerator 41 from second RFID tag 22. This allows server 50 to identify that medicine M stored in pharmaceutical refrigerator 41 is second medicine M2 delivered by second pharmaceutical distribution institution 20. Furthermore, server 50 can store the information in a state where it can be identified that second medicine M2 is a medicine delivered by individuals who are not the installer having installed pharmaceutical refrigerator 41, by means such as flagging the information about first medicine M1 while not flagging the information about second medicine M2 based on the installer information. In other words, server 50 can manage second medicine M2 delivered by second pharmaceutical distribution institution 20 as being identified as a medicine delivered by second pharmaceutical distribution institution 20, who is not the installer, based on the information received from pharmaceutical refrigerator 41 and second computer 21, as well as the installer information.

If necessary, server 50 may send the information about the status of second medicine M2 to second computer 21 (S215). This allows second pharmaceutical distribution institution 20 to know whether second medicine M2 is managed in medical institution 40 in an appropriate temperature environment, the quantity of second medicine M2 in stock, and the like, and to provide appropriate services to medical institution 40, without installing pharmaceutical refrigerator 41 by itself. The sending of information from server 50 to second computer 21 may be performed automatically or may be performed in response to a request from second computer 21. In the case where the sending of information is performed automatically, the sending may be performed every certain time or may be performed each time sliding door 45 is opened and closed, where it is highly likely that medicine M has been stored or retrieved.

Based on the installer information and the status of first medicine M1 in pharmaceutical refrigerator 41 and the status of second medicine M2 in pharmaceutical refrigerator 41, server 50 can calculate a fee for the operation of pharmaceutical refrigerator 41 to be borne by at least one of first pharmaceutical distribution institution 10, second pharmaceutical distribution institution 20, and medical institution 40 (S216). Specifically, if the distribution institution delivering medicine M stored in pharmaceutical refrigerator 41 is only first pharmaceutical distribution institution 10, who is the installer, medical institution may bear the full amount of the fee for the operation, or the fees or cost-sharing ratio can be calculated to be shared between the two, medical institution 40 and first pharmaceutical distribution institution 10. If second pharmaceutical distribution institution 20, who is not the installer, delivers medicine M stored in pharmaceutical refrigerator 41 in addition to first pharmaceutical distribution institution 10, who is the installer, the fees or cost-sharing ratio can be calculated to be shared among the three, medical institution 40, first pharmaceutical distribution institution 10, and second pharmaceutical distribution institution 20. For example, the amount borne by first pharmaceutical distribution institution 10 and the amount borne by second pharmaceutical distribution institution 20 can be calculated based on the ratio of the quantity of first medicine M1 and the ratio of the quantity of second medicine M2 to the quantity of medicine M stored in pharmaceutical refrigerator 41.

In other words, based on the beneficiary principle, the fees or cost-sharing ratio to be borne by the users of pharmaceutical refrigerator 41 can be calculated. Therefore, it is possible to suppress such a situation in which the cost burden regarding the installation and operation of pharmaceutical refrigerator 41 is unevenly applied to specific individuals. This can promote the spread and utilization of pharmaceutical refrigerator 41.

In pharmaceutical refrigerator operation support system 1 according to Embodiment 2, first printer 15, first scanner 17, second printer 25, and second scanner 27 are used. Therefore, information about first medicine M1, information about first RFID tag 12, information about second medicine M2, and information about second RFID tag 22 can be easily obtained.

The present disclosure should not be construed to be limited to the embodiments described above, and it should be understood that various changes may be made within the scope that does not depart from the gist thereof.

For example, in pharmaceutical refrigerator operation support system 1 according to Embodiment 1, the installer information may be used to calculate a fee for the operation of pharmaceutical refrigerator 41 to be borne by at least one of first pharmaceutical distribution institution 10, second pharmaceutical distribution institution 20, and medical institutions 40.

Moreover, in pharmaceutical refrigerator operation support system 1 according to Embodiment 2, first computer 11 and first printer 15, or second computer 21 and second printer 25 may be integrated. For example, first printer 15 may be configured to have the function of first computer 11 and to be able to communicate with server 50.

In addition, in pharmaceutical refrigerator operation support system 1 according to Embodiment 1 or Embodiment 2, either the combination of first printer 15 and first scanner 17 or the combination of second printer 25 and second scanner 27 may be used exclusively.

INDUSTRIAL APPLICABILITY

The pharmaceutical refrigerator operation support system, pharmaceutical refrigerator operation support method, and non-transitory computer-readable medium according to the present disclosure can be utilized for the distribution of medicine that requires strict temperature control.

The disclosure of Japanese Patent Application No. 2021-031797 filed on Mar. 1, 2021 including the specification, drawings and abstract is incorporated herein by reference in its entirety.

REFERENCE SIGNS LIST

1 Pharmaceutical refrigerator operation support system
10 First pharmaceutical distribution institution
11 First computer
12 First RFID tag
13 First label
14 First indication
15 First printer
16 First code
17 First scanner
20 Second pharmaceutical distribution institution
21 Second computer
22 Second RFID tag
23 Second label
24 Second indication
25 Second printer
26 Second code
27 Second scanner
30 Pharmaceutical institution
40 Medical institution
41 Pharmaceutical refrigerator
42 Cage
43 Communication apparatus
44 Operation display apparatus
45 Sliding door
50 Server
51 Processor
52 Memory

53 Communicator
M Medicine
M1 First medicine
M2 Second medicine

The invention claimed is:

1. A pharmaceutical refrigerator operation support system comprising: a server;

a pharmaceutical refrigerator that is installed in a medical institution, obtains radio frequency identification (RFID) information from an RFID tag attached to stored medicine, and sends, in response to detecting that a sliding door of the pharmaceutical refrigerator has been slid, information about a status of the stored medicine to the server including the RFID information;

a first computer that sends to the server information about a first medicine, information about a first RFID tag attached to the first medicine, and information about a first pharmaceutical distribution institution that delivers the first medicine to the medical institution; and a second computer that sends to the server information about a second medicine, information about a second RFID tag attached to the second medicine, and information about a second pharmaceutical distribution institution that delivers the second medicine to the medical institution, wherein:

the server manages a status of medicine in the pharmaceutical refrigerator by identifying the first medicine as a medicine delivered by the first pharmaceutical distribution institution and identifying the second medicine as a medicine delivered by the second pharmaceutical distribution institution, the identifying the first medicine is performed by matching the RFID information with the information about the first RFID tag, which has been received prior to receiving the RFID information to be matched, and registering, to a database of the server, the RFID information as corresponding to the first pharmaceutical distribution institution if the RFID information matches the information about the first RFID tag, and the identifying the second medicine is performed by matching the RFID information with the information about the second RFID tag, which has been received prior to receiving the RFID information to be matched, and registering, to the database of the server, the RFID information as corresponding to the second pharmaceutical distribution institution if the RFID information matches the information about the second RFID tag.

2. The pharmaceutical refrigerator operation support system according to claim 1, further comprising:

a first printer that prints the information about the first RFID tag on a first label having the first RFID tag;

a first scanner that reads the information about the first medicine from the first medicine, and reads the information about the first RFID tag from the first label;

a second printer that prints the information about the second RFID tag on a second label having the second RFID tag; and a second scanner that reads the information about the second medicine from the second medicine, and reads the information about the second RFID tag from the second label.

3. The pharmaceutical refrigerator operation support system according to claim 1, wherein:

the server

15 sends information about a status of the first medicine in the pharmaceutical refrigerator to the first computer, and sends information about a status of the second medicine in the pharmaceutical refrigerator to the second computer.

4. The pharmaceutical refrigerator operation support system according to claim 1, wherein:

the server obtains installer information indicating that an installer who has installed the pharmaceutical refrigerator is the first pharmaceutical distribution institution, and manages the status of the medicine in the pharmaceutical refrigerator by identifying the first medicine as a medicine delivered by the first pharmaceutical distribution institution, who is the installer, and identifying the second medicine as a medicine delivered by the second pharmaceutical distribution institution, who is not the installer, based on the RFID information received from the pharmaceutical refrigerator, the first computer, and the second computer, as well as the installer information.

5. The pharmaceutical refrigerator operation support system according to claim 4, wherein:

the server calculates a fee for operation of the pharmaceutical refrigerator to be borne by at least one of the first pharmaceutical distribution institution, the second pharmaceutical distribution institution, and the medical institution, based on the installer information, as well as a status of the first medicine in the pharmaceutical refrigerator and a status of the second medicine in the pharmaceutical refrigerator.

6. A pharmaceutical refrigerator operation support method comprising:

sending, by a first computer to a server, information about a first medicine, information about a first radio frequency identification (RFID) tag attached to the first medicine, and information about a first pharmaceutical distribution institution that delivers the first medicine to a medical institution;

sending, by a second computer to the server, information about a second medicine, information about a second RFID tag attached to the second medicine, and information about a second pharmaceutical distribution institution that delivers the second medicine to the medical institution;

obtaining, by a pharmaceutical refrigerator installed in the medical institution, RFID information from an RFID tag attached to medicine stored in the pharmaceutical refrigerator;

sending, by the pharmaceutical refrigerator to the server, in response to detecting that a sliding door of the pharmaceutical refrigerator has been slid, the RFID information; and managing, by the server, a status of medicine in the pharmaceutical refrigerator by identifying the first medicine as a medicine delivered by the first pharmaceutical distribution institution and identifying the second medicine as a medicine delivered by the second pharmaceutical distribution institution, wherein:

the identifying the first medicine is performed by matching the RFID information with the information about the first RFID tag, which has been received prior to receiving the RFID information to be matched, and registering, to a database of the server, the RFID information as corresponding to the first pharmaceutical distribution institution if the RFID information matches the information about the first RFID tag, and the identifying the second medicine is performed by matching the RFID information with the information about the second RFID tag, which has been received prior to receiving the RFID information to be matched, and registering, to the database of the server, the RFID information as corresponding to the second pharmaceutical distribution institution if the RFID information matches the information about the second RFID tag.

7. The pharmaceutical refrigerator operation support method according to claim 6, further comprising:

obtaining, by the server, installer information indicating that an installer who has installed the pharmaceutical refrigerator is the first pharmaceutical distribution institution, wherein, in the managing the status of the medicine in the pharmaceutical refrigerator by the server, the server manages the status of the medicine in the pharmaceutical refrigerator by identifying the first medicine as a medicine delivered by the first pharmaceutical distribution institution, who is the installer, and identifying the second medicine as a medicine delivered by the second pharmaceutical distribution institution, who is not the installer, based on information received from the first computer, the second computer, and the pharmaceutical refrigerator, as well as the installer information.

8. The pharmaceutical refrigerator operation support method according to claim 7, further comprising:

calculating, by the server, a fee for operation of the pharmaceutical refrigerator to be borne by at least one of the first pharmaceutical distribution institution, the second pharmaceutical distribution institution, and the medical institution, based on the installer information, as well as a status of the first medicine in the pharmaceutical refrigerator and a status of the second medicine in the pharmaceutical refrigerator.

9. A non-transitory computer-readable medium storing a computer program executed by a server communicably connected via a network to a pharmaceutical refrigerator that is installed in a medical institution and that stores medicine delivered by a first pharmaceutical distribution institution and a second pharmaceutical distribution institution, the computer program causing the server to execute:

receiving, from a first computer, information about a first medicine, information about a first radio frequency identification (RFID) tag attached to the first medicine, and information about the first pharmaceutical distribution institution;

receiving, from a second computer, information about a second medicine, information about a second RFID tag attached to the second medicine, and information about the second pharmaceutical distribution institution;

receiving, from the pharmaceutical refrigerator, RFID information obtained from an RFID tag affixed to medicine stored in the pharmaceutical refrigerator, wherein the information is transmitted from the pharmaceutical refrigerator detecting that a sliding door of the pharmaceutical refrigerator has been slid; and managing a status of medicine in the pharmaceutical refrigerator by identifying the first medicine as a medicine delivered by the first pharmaceutical distribution institution and identifying the second medicine as a medicine delivered by the second pharmaceutical distribution institution, wherein:

the identifying the first medicine is performed by matching the RFID information with the information about the first RFID tag, which has been received prior to receiving the RFID information to be matched, and registering, to a database of the server, the RFID information as corresponding to the first pharmaceutical distribution institution if the RFID information matches the information about the first RFID tag, and the identifying the second medicine is performed by matching the RFID information with the information about the second RFID tag, which has been received prior to receiving the RFID information to be matched, and registering, to the database of the server, the RFID information as corresponding to the second pharmaceutical distribution institution if the RFID information matches the information about the second RFID tag.

10. The non-transitory computer-readable medium according to claim 9, wherein the computer program causes the server to further execute:

obtaining installer information indicating that an installer who has installed the pharmaceutical refrigerator is the first pharmaceutical distribution institution, wherein, in the managing the status of the medicine in the pharmaceutical refrigerator by the server, the server is caused to execute managing the status of the medicine in the pharmaceutical refrigerator by identifying the first medicine as a medicine delivered by the first pharmaceutical distribution institution, who is the installer, and identifying the second medicine as a medicine delivered by the second pharmaceutical distribution institution, who is not the installer, based on the RFID information received from the first computer, the second computer, and the pharmaceutical refrigerator, as well as the installer information.

11. The non-transitory computer-readable medium according to claim 10, wherein the computer program causes the server to further execute:

calculating a fee for operation of the pharmaceutical refrigerator to be borne by at least one of the first pharmaceutical distribution institution, the second pharmaceutical distribution institution, and the medical institution based on the installer information, as well as a status of the first medicine in the pharmaceutical refrigerator and a status of the second medicine in the pharmaceutical refrigerator.

* * * * *